United States Patent [19]

Thottathil et al.

[11] Patent Number: 5,594,153
[45] Date of Patent: Jan. 14, 1997

[54] PROCESS FOR THE PREPARATION OF 1,3-DIOXANE DERIVATIVES USEFUL IN THE PREPARATION OF HMG-COA REDUCTASE INHIBITORS

[75] Inventors: John K. Thottathil, Robbinsville; Yadagiri Pendri, Old Bridge; Wen-Sen Li, Lincroft, all of N.J.; David R. Kronenthal, Yardley, Pa.

[73] Assignee: E. R. Squibb & Sons, Inc., Princeton, N.J.

[21] Appl. No.: 498,493

[22] Filed: Jul. 5, 1995

Related U.S. Application Data

[62] Division of Ser. No. 135,604, Oct. 8, 1993, Pat. No. 5,457,227, which is a division of Ser. No. 858,907, Mar. 27, 1992, Pat. No. 5,278,313.

[51] Int. Cl.$^6$ .................................................. C07D 319/06
[52] U.S. Cl. ........................................... 549/374; 549/375
[58] Field of Search ..................................... 549/374, 375

[56] References Cited

U.S. PATENT DOCUMENTS

| | | | |
|---|---|---|---|
| 4,571,428 | 2/1986 | Kapa | 556/437 |
| 4,613,610 | 9/1986 | Wareing | 514/406 |
| 4,650,890 | 3/1987 | Jewell, Jr et al. | 556/446 |
| 4,824,959 | 4/1989 | Han et al. | 548/253 |
| 4,870,187 | 9/1989 | Sit et al. | 548/253 |
| 4,870,199 | 9/1989 | Chen et al. | 556/437 |
| 4,897,490 | 1/1990 | Sit et al. | 548/253 |
| 4,898,950 | 2/1990 | Han et al. | 548/253 |
| 4,970,313 | 11/1990 | Wess et al. | 544/335 |
| 4,977,279 | 12/1990 | Wess et al. | 548/274 |
| 4,983,759 | 1/1991 | Inoue et al. | 560/174 |
| 4,994,602 | 2/1991 | Seido et al. | 560/186 |

FOREIGN PATENT DOCUMENTS

| | | |
|---|---|---|
| 2662688 | 6/1989 | Australia. |
| 0319847 | 6/1989 | European Pat. Off. . |
| 0374922 | 6/1990 | European Pat. Off. . |

OTHER PUBLICATIONS

Mancuso, et al., "Oxidation of Long–Chain and Related Alcohols to Carbonyls by Dimethyl Sulfoxide Activated by Oxalyl Chloride", J. Org. Chem., vol. 43, No. 12, pp. 2480–2482 (1978).

Lee et al., "A General Method for the Synthesis of syn–E–3,5–Dihydroxy–6–heptenoates", Synlett Letters, p. 508 (1991).

Evans et al., "Synthesis of 1,3–Diol Synthons from Epoxy Aromatic Precursors: An Approach to the Construction of Polyacetate–Derived Natural Products", J. Org. Chem., 56, pp. 741 – 750 (1991).

Cardani et al., "Synthesis of Enantiomeric Pure Intermediate for the Lactone Portion of Compactin and Mevinolin", Tetrahedron, vol. 46, No. 20, pp. 7283 – 7288 (1990).

*Primary Examiner*—David B. Springer
*Attorney, Agent, or Firm*—Burton Rodney

[57] ABSTRACT

A novel, overall process for the preparation of a compound of the formula I:

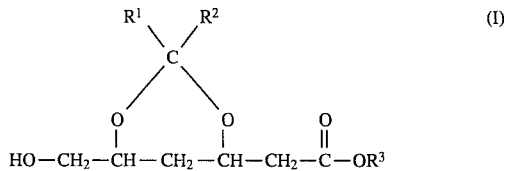

where $R^1$ and $R^2$ are each independently hydrogen, an alkyl group, a cycloalkyl group, an aryl group or, taken together with the carbon atom to which they are attached, form a cycloalkyl group; and $R^3$ is hydrogen, an alkyl group, or an aryl group, or salts thereof, useful as intermediates in the preparation of HMG-CoA reductase inhibitors; novel methods within the overall process; and novel intermediates produced by those methods.

11 Claims, No Drawings

PROCESS FOR THE PREPARATION OF 1,3-DIOXANE DERIVATIVES USEFUL IN THE PREPARATION OF HMG-COA REDUCTASE INHIBITORS

This is a division of application Ser. No. 08/135,604, filed Oct. 8, 1993, U.S. Pat. No. 5,457,227 which is a division of application Ser. No. 07/585,907, filed Mar. 27, 1992, U.S. Pat. No. 5,278,313.

FIELD OF THE INVENTION

The present invention relates to a process for the preparation of 1,3-dioxane derivatives useful in the preparation of HMG-CoA reductase inhibiting compounds. The instant invention also relates to the novel intermediates produced.

SUMMARY OF THE INVENTION

The instant invention provides a process for the preparation of compounds of the formula I:

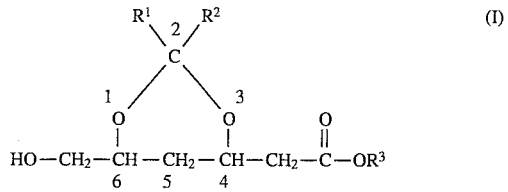

where
R$^1$ and R$^2$ are each independently hydrogen, an alkyl group, a cycloalkyl group, an aryl group or, taken together with the carbon atom to which they are attached, form a cycloalkyl group; and R$^3$ is hydrogen, an alkyl group or an aryl group; and salts thereof, and especially for the preparation of optically active such compounds.

Compounds of the formula I are useful as intermediates in the preparation of inhibitors of the enzyme 3-hydroxy-3-methylglutaryl coenzyme A (HMG-CoA) reductase, which inhibitors are useful, for example, in the treatment of hypercholesterolemia, hyperlipoproteinemia, hyperlipodemia and atherosclerosis. The instant invention provides a convenient process for the preparation of compounds of the formula I in good yields, particularly for the preparation of chiral compounds of the formula I having the 4R,6S configuration which are preferred in the preparation of HMG-CoA reductase inhibitors.

The process of the instant invention comprises the steps of:

(a) condensing a compound of the formula II:

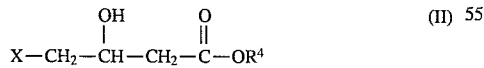

where
X is a halogen atom; and
R$^4$ is an alkyl group, a cycloalkyl group or an aryl group,
with a compound of the formula III, or a salt thereof:

where

R$^3$ is as defined above for the formula I; in the presence of a condensation agent, to form a compound of the formula IV, or a salt thereof:

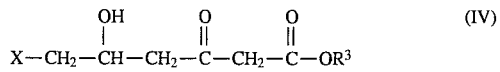

where X is as defined in formula II and R$^3$ is as defined in formula I;

(b) reducing, in the presence of a reducing agent, the compound of the formula IV or salt thereof prepared in step (a) to form a compound of the formula V, or a salt thereof:

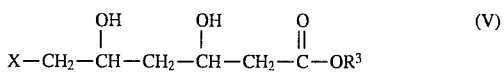

where X is as defined in formula II and R$^3$ is as defined in formula I;

(c) preparing a compound of the formula VII, or a salt thereof:

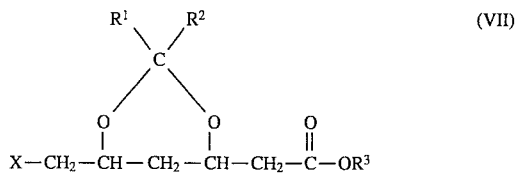

where
R$^1$ R$^2$ and R$^3$ are as defined in formula I; and
X is as defined in formula II, by reacting the compound of formula V or salt thereof prepared in step (b) with a compound of the formula VIa, VIb or VIc:

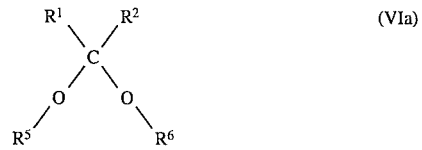

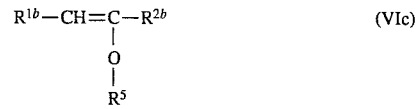

where
R$^1$ and R$^2$ are as defined in the formula I;
R$^{1b}$ and R$^{2b}$ are each independently hydrogen, an alkyl group, a cycloalkyl group, an aryl group or, taken together with the carbon atoms to which they are attached, form a 1,2-cycloalkenyl group; and
R$^5$ and R$^6$ are each independently an alkyl group, in the presence of an acidic condensation agent;

(d) preparing a compound of the formula VIII, or a salt thereof:

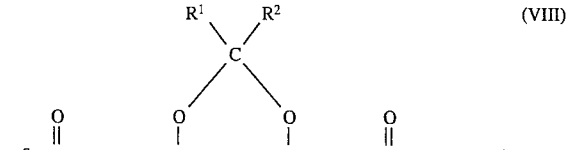

where
R$^1$, R$^2$ and R$^3$ are as defined in formula I; and

R[7] an alkyl group or an aryl group, by displacing the group X of the compound of the formula VII or salt thereof prepared in step (c) with an acyloxy group of the formula —O—C(O)—R[7] by use of a displacement agent; and (e) hydrolyzing the compound of the formula VIII or salt thereof prepared in step (d) to produce the compound of the formula I or a salt thereof.

DETAILED DESCRIPTION OF THE INVENTION

The instant invention provides a novel, overall process for the preparation of compounds of the formula I or salts thereof comprising the steps (a) through (e) set forth above. In addition, the instant invention provides the individual methods of each of steps (a) through (e) which are novel methods, and the novel intermediates of the formulae IV, V, VII and VIII or salts thereof formed therein, as described following. In the following description, reference to a compound of a designated formula includes compounds of that structure or salts thereof unless otherwise specified. As used in this specification, reference to a compound of a designated formula or salt thereof is defined to include solvates, such as hydrates, of said compound or salt.

In step (a), a compound of the formula IV:

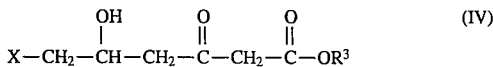

is prepared by a method wherein a compound of the formula II:

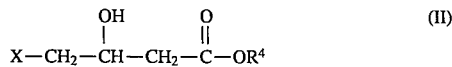

is condensed with a compound of the formula III:

in the presence of a condensation agent. In the formulae II, III and IV, $R^3$ is preferably a lower alkyl group such as t-butyl, $R^4$ is preferably a lower alkyl group such as methyl or ethyl, and X is preferably a bromine or, particularly, a chlorine atom.

The starting materials of the formulae II and III of the method of step (a) may be prepared by one of ordinary skill in the art. For example, the compounds of the formula II may be prepared by a method such as that described in U.S. application Ser. No. 07/693,893, filed May 1, 1991 by Patel et al., incorporated herein by reference. The compounds of the formula III are readily available commercial products and/or may be prepared by methods well known to one of ordinary skill in the art.

Any compound effecting the reaction of step (a) may be employed as the condensation agent. Basic condensation agents are preferred. It is particularly preferred to employ a basic metallic condensation agent such as $NaNH_2$, potassium hexamethyldisilazide (KHMDS), $KNH_2$, a lithium amide compound such as lithium diisopropylamide (LDA) or lithium dicyclohexylamide (LiDCYA), or any other such bases. Lithium hexamethyldisilazide (LiHMDS) is particularly preferred.

The method of step (a) is preferably conducted at a temperature of from about 25° C. to about −90° C., most preferably from about −40° C. to about −78° C. The reaction of step (a) is preferably conducted under an inert atmosphere such as nitrogen or argon.

It is preferred to employ amounts of starting materials such that the molar ratio of the compound of the formula III to the compound of the formula II is from about 8:1 to about 3:1, most preferably from about 4:1 to about 3.5:1; and the molar ratio of the condensation agent to the compound of the formula II is from about 8:1 to about 3:1, most preferably from about 4:1 to about 3.5:1. Solvents are preferably employed which are selected from organic solvents such as ether, hexanes, dioxane, toluene, cyclohexane, or any other inert organic solvent. The organic solvent is most preferably tetrahydrofuran.

The method of step (a), and compounds of the formula IV, are novel.

In the method of step (b), a compound of the formula V:

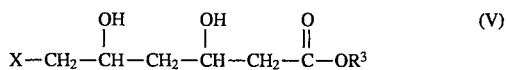

is prepared by reducing the compound of the formula IV prepared in step (a) above by use of a reducing agent.

Any reducing agent effecting the reaction of step (b) may be employed. Exemplary reducing agents include sodium borohydride, zinc borohydride, lithium borohydride, diisobutylaluminum hydride, sodium bis(2-methoxyethoxy)aluminum hydride or similar hydride reducing agents and agents effecting catalytic hydrogenation such as hydrogen/catalyst combinations where the catalyst is, for example, Raney nickel, platinum, rhodium, palladium or palladium hydroxide (Pd(OH)2), any of which may be employed alone, in oxide form (for example, $PtO_2$), or on a carbon support (for example, Pd on carbon, Pt on carbon, $PtO_2$ on carbon or $Pd(OH)_2$ on carbon).

It is preferred, in step (b), to prepare a compound of the formula V having the preferred stereoisomeric configuration of formula Va:

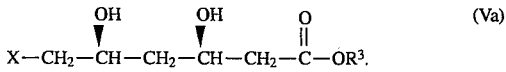

Stereospecificity of the reduction reaction may be achieved by the use of a hydride reducing agent. Particularly high stereospecificity may be achieved by the use of a combination of sodium borohydride and a trialkylborane or alkylalkoxyborane such as an alkoxydialkylborane. The reducing agent employed is most preferably a mixture of a trialkylborane such as triethylborane or an alkoxydialkylborane such as methoxydiethylborane, and sodium borohydride.

The stereospecific reduction is preferably carried out by sequential addition of borane reagent followed by sodium borohydride. At the end of the reduction, the formed boron complex may be hydrolyzed by a peroxide such as hydrogen peroxide in the presence of a base such as sodium hydroxide to obtain compounds of the formula Va.

The method of step (b) is preferably conducted at a temperature of from about −30° C. to about −90° C., most preferably from about −60° C. to about −80° C. The reaction of step (b) is preferably conducted under an inert atmosphere such as nitrogen or argon.

Molar ratios of reducing agent to the starting compound of the formula IV are preferably from about 1:1 to about 4:1, particularly those from about 2:1 to about 4:3. Solvents are preferably employed which are selected from inert organic solvents such as tetrahydrofuran, ether, dioxane and the like, in combination with an alcoholic solvent such as methanol, ethanol and the like, most preferably a mixture of tetrahydrofuran and methanol.

The method of step (b), and the compounds of the formula V, are novel.

In the method of step (c), a compound of the formula VII:

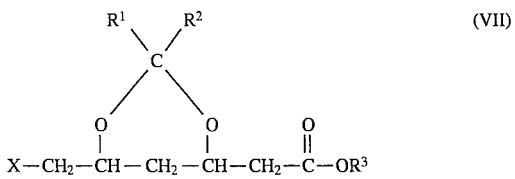

is prepared by reacting the compound of the formula V prepared in step (b) above with a compound of the formula VIa, VIb or VIc:

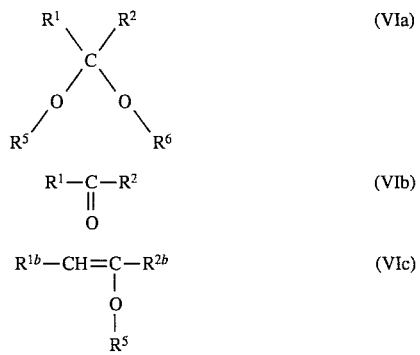

in the presence of an acidic condensation agent.

In the above formulae, $R^1$ and $R^2$ are preferably a lower alkyl group such as methyl, $R^{1b}$ is preferably hydrogen and $R^{2b}$ is preferably a lower alkyl group such as methyl, and $R^5$ and $R^6$ are preferably the same or different lower alkyl group, such as methyl or ethyl. $R^5$ and $R^6$ are most preferably both methyl. The starting compounds of the formulae VIa, VIb and VIc are readily available, or may be prepared by methods well known to the skilled artisan.

Any organic or mineral acid which effects the reaction of step (c) may be employed as the condensation agent. Exemplary acidic condensation agents include acidic polymeric resins, p-toluenesulfonic acid, methanesulfonic acid, pyridinium p-toluene sulfonate, hydrochloric and sulfuric acids, cupric sulfate, cupric bromide and the like and, particularly, camphorsulfonic acid (CSA). When water is formed in the condensation reaction of step (c) distillation, or a drying agent or molecular sieve, may be employed to facilitate removal thereof.

The method of step (c) is preferably conducted at a temperature of from about 0° C. to about 60° C., most preferably from about 10° C. to about 30° C. The reaction of step (c) is preferably conducted under an inert atmosphere such as nitrogen or argon.

Molar ratios of the starting materials are preferably selected so that the molar ratio of the compound of the formula VIa, VIb or VIc employed to the compound of the formula V is from about 1:1 to about 20:1, most preferably from about 3:1 to about 5:1. The molar ratio of acidic condensation agent to the compound of the formula V is preferably from about 1:1 to about 0.001:1, most preferably from about 0.01:1 to about 0.05:1. The reaction of step (c) is preferably conducted without the addition of solvent, although solvents such as toluene, chloroform and the like, preferably dichloromethane, may be employed.

The method of step (c) and the compounds of the formula VII, are novel.

In the method of step (d), a compound of the formula VIII:

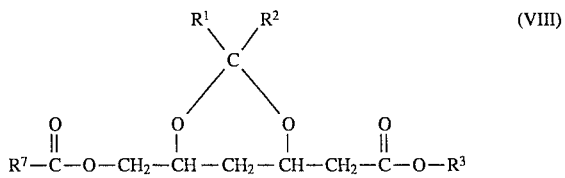

is prepared by displacing the group X of the compound of the formula VII prepared in step (c) above With an acyloxy group of the formula —O—C(O)—$R^7$ by use of a displacement agent.

Any displacement agent effecting the reaction of step (d) may be employed. Exemplary acyloxy displacement agents are those of the formula IX:

where $R^7$ is as defined in the formula VIII and M is a metal, preferably an alkali metal, such as sodium, cesium or potassium; or an ammonium group, such as an alkyl ammonium group. The compounds of formula IX are known and may be prepared by methods known to the skilled artisan. It is particularly preferred to employ displacement agents having the formula IXa:

where $R^7$ is as defined in the formula VIII and $R^8$ is an alkyl group, preferably a lower alkyl group such as n-butyl.

The method of step (d) is preferably conducted at a temperature o f from about 0° C. to about 130° C., most preferably from about 50° C. to about 120° C. The reaction of step (d) is preferably conducted under an atmosphere of inert gas such as argon.

Molar ratios of the starting materials are preferably selected so that the molar ratio of the compound of the formula IX or IXa to the compound of the formula VII is from about 1:1 to about 5:1, most preferably from about 2:1 to about 3:1. Solvents are preferably employed which are selected from inert organic solvents, such as dimethylformamide, acetonitrile, dimethylsulfoxide, or dimethylacetamide, most preferably N-methylpyrrolidinone.

The method of step (d) is novel. Further, compounds of the formula VIII where $R^7$ is an alkyl group are novel, and are preferably prepared by the instant method. Use of compounds of the formula VIII having as $R^7$ an alkyl group, most preferably a lower alkyl group such as methyl, facilitates the hydrolysis procedure of step (e) described below. In particular, the by-products formed by the use of such compounds in step (e), such as methyl acetate or acetic acid, are volatile and are readily separated from the desired compound of the formula I relative to the by-products formed when a compound of the formula VIII where $R^7$ is aryl is employed.

In the method of step (e), a compound of the formula I is prepared by hydrolyzing the compound of the formula VIII prepared in step (d) above. Any hydrolyzing agent effecting the reaction of step (e) may be employed. Exemplary hydrolyzing agents are basic compounds such as alkali metal hydroxides (for example, sodium hydroxide, potassium hydroxide or lithium hydroxide), or any other hydroxide base. Potassium carbonate is particularly preferred as the hydrolyzing agent. The molar ratio of hydrolyzing agent to the compound of the formula VIII is preferably from about 2:1 to about 1:2, most preferably from about 1:1 to about 1:2.

Use of a mildly basic medium is particularly advantageous in step (e). A "mildly basic medium", as used in this specification, denotes a reaction medium at a pH which selectively hydrolyzes the $R^7$—C(O)—O—ester group of the compound of the formula VIII, relative to hydrolysis of the $R^3$—O—C(O)—ester group. Preferably, a pH of from about 7 to about 12, most preferably from about 8 to 10, is employed. It is particularly desirable to employ a medium such that substantially all of the product formed in step (e) is the compound of the formula I, for example, an amount greater that about 99% of the product formed.

It is further preferred to employ a mild base to achieve the mildly basic medium described above. As used in this specification, a "mild base" is a base having a pKa of from about 5 to about 12, most preferably from about 6 to about 10. Exemplary mild bases include alkali metal carbonates such as sodium carbonate, and particularly potassium carbonate as discussed above. pKa may be determined by the method described in Cookson, Chem. Rev., 74, 5–28 (1974).

In addition to allowing selective hydrolysis, use of a mild base and mildly basic medium is advantageous in avoiding instability of the compound of formula I, for example, elimination of the group —O—C($R^1$)($R^2$)—O—(ring opening), which may occur under strongly basic conditions.

The method of step (e) is preferably conducted at a temperature of from about 0° C. to about 100° C., most preferably from about 10° C. to about 40° C. Alcoholic solvents are preferably employed, exemplified by alkanols such as methanol.

The method o f step (e) is novel where (i) a mild base or mildly basic medium is employed and/or (ii) a compound of the formula VIII is employed where $R^7$ is an alkyl group. Use of a compound of the formula VIII where $R^7$ is an alkyl group is particularly advantageous for the reasons described above.

Exemplary compounds falling within the scope of the present invention include:

(S)-6-chloro-5-hydroxy-3-oxohexanoic acid, 1,1-dimethylethyl ester (formula IV);

(S)-6-bromo-5-hydroxy-3-oxohexanoic acid, 1,1-dimethylethyl ester (formula IV);

(R,S) -6-chloro-3,5-dihydroxyhexanoic acid, 1,1-dimethylethyl ester (formula V);

(R,S) -6-bromo-3,5-dihydroxyhexanoic acid, 1,1-dimethylethyl ester (formula V);

(4R-cis)-6-(chloromethyl)-2,2-dimethyl-1,3-dioxane-4-acetic acid, 1,1-dimethylethyl ester (formula VII);

(4R-cis)-6-(bromomethyl)-2,2-dimethyl-1,3-dioxane-4-acetic acid, 1,1-dimethylethyl ester (formula VII);

(4R-cis)-6-[(acetyloxy)methyl]-2,2-dimethyl-1,3-dioxane-4-acetic acid, 1,1-dimethylethyl ester (formula VIII);

(4R-cis)-6-[(benzoyloxy)methyl]-2,2-dimethyl-1,3-dioxane-4-acetic acid, 1,1-dimethylethyl ester (formula VIII); and (4R-cis) -6 -(hydroxymethyl)-2,2 -dimethyl-1,3-dioxane-4-acetic acid, 1,1-dimethylethyl ester (formula I).

In each of the above steps (a) through (e), solvates, as well as the salt or free form of the compounds, may be employed as starting materials or prepared as products. Solvates may be organic solvates or, preferably, hydrates. Salts include acidic or basic salts with inorganic or organic acids or bases. Exemplary salts include salts formed with nontoxic cations such as alkali metal (for example, sodium, potassium or lithium) or alkaline earth metal (for example, calcium or magnesium) cations or ammonium salts formed with nontoxic amines such as trialkylamines, dibenzylamine, pyridine, N-methylmorpholine, N-methylpiperidine and the like.

The term "alkyl", as used in this specification, preferably denotes a straight or branched saturated carbon chain having from 1 to 21 carbon atoms. Exemplary alkyl groups include methyl, ethyl, i-propyl, n-propyl, t-butyl and n-butyl.

The term "lower alkyl", as used in this specification, preferably denotes an alkyl group as described above having from 1 to 8, most preferably 1 to 6, carbon atoms.

The term "cycloalkyl", as used in this specification, preferably denotes a saturated carbocyclic ring system having from 1 to 3 rings and from 3 to 21 carbon atoms. Exemplary cycloalkyl groups include cyclopentyl, cyclohexyl and cycloheptyl.

The term "cycloalkenyl", as used in this specification, preferably denotes a partially unsaturated carbocyclic ring system having from 1 to 3 rings and from 3 to 21 carbon atoms. Exemplary cycloalkenyl groups include cyclopentenyl, cyclohexenyl and cycloheptenyl.

The term "aryl", as used in this specification, preferably denotes an unsaturated monocyclic or bicyclic carbocyclic ring system having from 6 to 12 carbon atoms. Exemplary aryl groups include phenyl, biphenyl and naphthyl.

Each of the alkyl (including lower alkyl), cycloalkyl, cycloalkenyl or aryl groups described above may optionally be substituted. Appropriate substituents include those groups allowing preparation according the methods of the present invention. For example, the cycloalkyl, cycloalkenyl or aryl groups described above may be substituted by one or more alkyl groups.

The term "halogen", as used in this specification, denotes fluorine, iodine or preferably, bromine or chlorine.

The present invention contemplates preparation of any of the compounds herein which may be in the form of mixtures of stereoisomers (e.g. racemates), mixtures of selected stereoisomers, and individual stereoisomers substantially free of other isomers. Mixtures of isomers may be separated into individual isomers according to methods which are known to the skilled artisan, for example, by fractional crystallization, fractional distillation, adsorption chromatography or other suitable separation processes. Resulting racemates may be separated into antipodes by introduction of suitable salt-forming groupings, e.g. by forming a mixture of diastereoisomeric salts with optically active salt-forming agents, separating the mixture into diastereoisomeric salts and converting the separated salts into the free compounds. The enantiomeric forms may also be separated by fractionation through chiral high pressure liquid chromatography columns. Most preferably, chiral compounds may be prepared directly by the selective stereoisomeric methods for preparation provided by the instant invention and described above.

In the preparation of inhibitors of HMG-CoA reductase having a preferred stereoisomeric configuration, it is desirable to employ chiral intermediates. In this regard, the compounds of formula I contain two asymmetric carbon atoms indicated by an asterisk as follows:

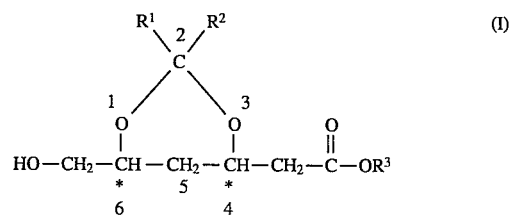

The compounds of the formulae V, VII and VIII also contain the above asymmetric carbon atoms at the analogous positions. The four stereoisomers resulting from the above asymmetric carbon atoms in the compounds of the formula I are designated as follows:

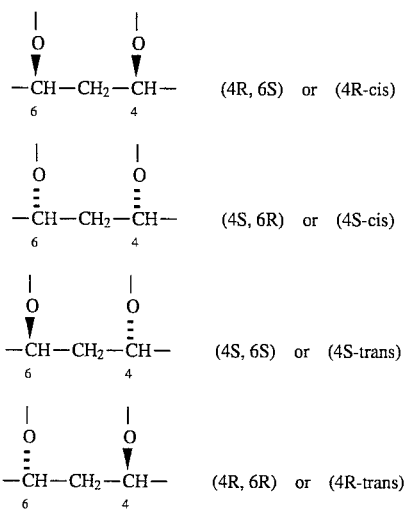

Compounds having the (4R-cis), that is, the following stereoisomeric configurations, are preferably prepared by the methods of the instant invention:

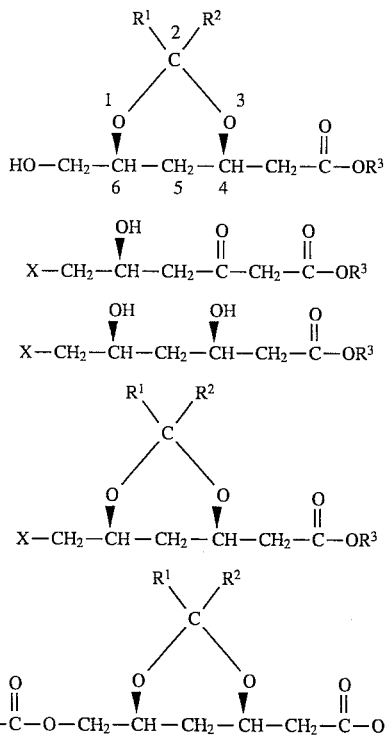

Compounds of the above formulae may be prepared selectively, and, preferably, substantially free of other isomers, by employing a starting material of the formula II having the stereoisomeric configuration IIa:

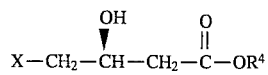

and by employing the stereoselective methods of steps (a) through (e) described above.

The compounds of the formula I prepared as described herein may be employed in the preparation of inhibitors of the enzyme HMG-CoA reductase. Exemplary such inhibitors, and methods of preparation thereof, are described in U.S. Pat. No. 4,898,950, incorporated herein by reference.

It is particularly preferred to prepare HMG-CoA reductase inhibitors of the formula X:

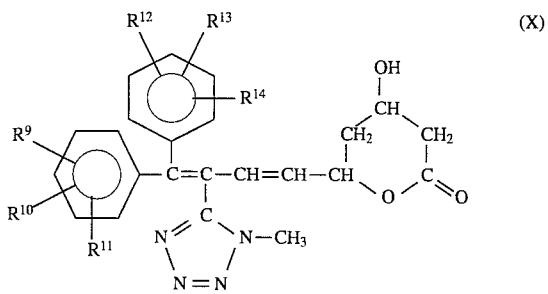

where $R^9$ and $R^{12}$ are each independently hydrogen, halogen, $C_{1-4}$ alkyl, $C_{1-4}$ alkoxy or trifluoromethyl (preferably, where both $R^9$ and $R^{12}$ are fluorine); and $R^{10}$, $R^{11}$, $R^{13}$ and $R^{14}$ are each independently hydrogen, halogen, $C_{1-4}$ alkyl or $C_{1-4}$ alkoxy (preferably where all are hydrogen);

or salts thereof, which compounds are described in U.S. Pat. No. 4,898,950.

For example, a compound of the formula I or a salt thereof may be oxidized according to known methods, such as those described in A. J. Mancuso, S-L. Huang and D. Swern, J. Org. Chem., 43, No. 12, 2480–2482 (1978), by use of a Swern oxidation reaction (oxalyl chloride in dimethylsulfoxide, with the addition of triethylamine) to yield a compound of the formula XI, or a salt thereof:

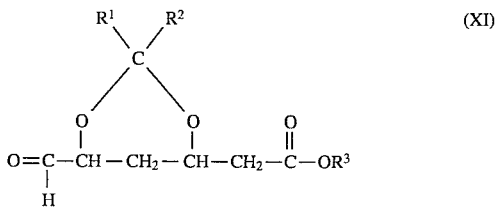

wherein $R^1$, $R^2$ and $R^3$ are as defined in the formula I, and the latter compound employed in the preparation of a compound of the formula X or a salt thereof according to the methods described in the aforementioned U.S. Pat. No. 4,898,950.

The following examples are provided to further illustrate the instant invention, and should not be construed as limiting the scope of the instant claims.

EXAMPLE 1

Preparation of (4R-cis)-6-(Hydroxymethyl)-2,2-dimethyl-1,3-dioxane-4-acetic acid, 1,1-dimethylethyl ester (a) (S)-4-Chloro-3-hydroxybutanoic acid methyl ester

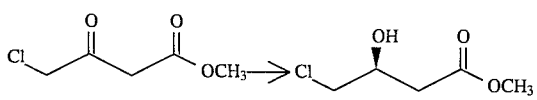

4-Chloro-3-oxobutanoic acid methyl ester was converted to the title compound according to the fermentation procedures described in U.S. patent application Ser. No. 07/693,893, filed May 1, 1991 by Patel et al.

The filtered fermentation batch (390 L, 1193.0 g by BPD) of the chlorohydrin so prepared was extracted with 570 L (2×) of ethyl acetate, and the phases were separated, concentrated and distilled yielding 1079 g (90.4%) of the crude title product (b.p. 50°–100° C./3–5 mmHg). The weight of the residue was 417 g. The crude product was fractionated in the laboratory on a 2.5×25 cm helix-filled column.

| Fractions | |
|---|---|
| 1. b.p. 80–90° C./ 4.0 – 4.5 mmHg | 47.0 g |
| 2. b.p. 90–93° C./ 4.0 – 3.5 mmHg | 843.3 g |
| 3. residue: | 94.7 g |
| Total | 985.0 g |
| Title Product (fraction 2) | 843.0 g |
| 78.1% yield (from crude) | |
| 70.7% recovery from the broth | |

(b) (S)-6-Chloro-5-hydroxy-3-oxohexanoic acid, 1,1-dimethylethyl ester

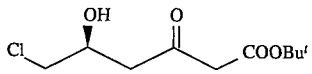

A flame-dried 5 L three-necked round bottomed flask was charged with tetrahydrofuran (THF) (distilled, 500 ml) and lithium hexamethyl-disilazide (1.715 L, 3.5 eq, 1M solution in THF) at −78° C. The THF was added to prevent the LiHMDS from precipitation. To this light brown solution was slowly added tert-butyl acetate (CH₃CO₂Buᵗ) (266 ml, 4.0 eq) over a period of 10 minutes at −78° C. At the end of the addition, the solution was stirred for another 40 minutes at −78° C.

To this light brown homogeneous reaction mixture was added a solution of (S)-4-chloro-3hydroxybutanoic acid methyl ester, prepared in step (a) above and employed without further purification (75 g, 0.493 mole), in 60 ml THF over a period of 15 minutes. The addition was slightly exothermic. The internal temperature climbed from −78° C. to −74° C. during the addition.

The reaction was stirred at −78° C. for 1 hour, then at −50° C. for 1 hour. At this point thin-layer chromatography (TLC) indicated complete reaction (TLC: silica gel; Ethyl acetate (EtOAc):Hexane; 1:1; $R_f$=0.56, UV visualization for title compound; $R_f$=0.55, PMA visualization for starting material, (S)-4-chloro-3-hydroxybutanoic acid methyl ester). The reaction was quenched by the slow addition of acetic acid (AcOH) (200 ml) with vigorous stirring over a period of 30 –40 minutes. The reaction mixture became heterogeneous due to the freezing of acetic acid. During the quench, the internal temperature was maintained between −50° C. and −40° C. The cooling bath was removed and the reaction was slowly allowed to warm to 0° C. The resulting thick yellow solution was poured into a mixture of ethyl acetate (EtOAc) (1 L) and H₂O (deionized, 1L) in a separatory funnel. The aqueous layer was separated and extracted with EtOAc (300 ml×2). The combined EtOAc layer was washed with 1N HCl (500 ml×2 ), and half-saturated NaCl (500 ml×1). The combined HCl and NaCl washings were extracted with EtOAc (300 ml×1). All of the EtOAc extracts were then combined and washed with saturated NaHCO₃ (500 ml×2), half-saturated NaCl (500 ml×1 ) and brine (500 ml×2 ), dried over Na₂SO₄, filtered and concentrated to give 136.74 g of the title compound as a brown oil (approximately 100%). H-NMR indicated that no starting material remained. The product was approximately 90% pure by H-NMR, and TLC (the same conditions as previously described) showed a major spot and two minor impurities (<5%). The product was used for the next step without any further purification.

(c) (R,S)-6-Chloro-3,5-dihydroxyhexanoic acid, 1,1-dimethylethyl ester

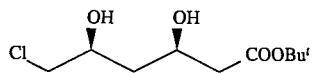

The crude hydroxyketone (S)-6-chloro-5-hydroxy-3-oxohexanoic acid, 1,1-dimethylethyl ester (66.0 g) obtained in step (b) above was dissolved in THF (1.25 L) and HPLC grade methanol (MeOH) (630 ml) at −78° C. To this brown solution was added methoxydiethylborane (Et₂BOMe) (285 ml, 1M solution in THF) over a period of 20 minutes. The addition was slightly exothermic and the solution became cloudy. At the end of the addition, the reaction solution was stirred for an additional 20 minutes. To this cloudy solution was added solid NaBH₄ (11 g, 1.15 eq) portionwise over a period of 35 minutes. The addition generated a large mount of hydrogen gas. Good stirring was used to prevent frothing.

The resulting suspension was stirred at −78° C. for 4 hours, and then quenched by the dropwise addition of acetic acid (70 ml) over a period of 10 minutes. The solution was warmed to 0° C. and diluted with ethyl acetate (EtOAc) (1.25 L), washed with half-saturated NaCl (500 ml×2) and saturated NaHCO₃ (500 ml×4). The combined aqueous washings were back-extracted with EtOAc (500 ml×2 ). All of the EtOAc extracts were combined and washed with half-saturated aqueous NaCl (500 ml×1), brine (500 ml×2), dried over Na₂SO₄, filtered, and concentrated to give 69.4 g of the crude title product as a mixture of the diol (R,S)-6-chloro-3,5-dihydroxyhexanoic acid, 1,1-dimethylethyl ester and the corresponding boron complex. At this point, the boron complex was the major component in the crude residue, and about 2.6% of the starting material remained by H-NMR. (TLC: silica gel; EtOAc: Hexane; 1:1; $R_f$=0.71, for the boron complex; $R_f$=0.44, for the diol; $R_f$=0.56, for the starting material.)

The above crude product (69.4 g) was dissolved in THF (350 ml) and water (140 ml, pH 9, deionized). The pH of the deionized water was adjusted to 9 by the addition of 1N NaOH. To this solution was added dropwise 30% aqueous H₂O₂ (17.5 ml) over a period of 20 minutes with an ice-water cooling. The addition of H₂O₂ was exothermic and ice-water cooling was employed to control the temperature between 24° C. and 30° C. The pH of the resulting solution was approximately 6. The reaction was stirred for an additional 30 minutes at room temperature. Then, the solution was titrated with 1N NaOH from pH 6 to pH 7 (about 0.6 ml) and stirred for an additional 30 minutes. (Maintaining a pH of 7 during the stirring period is preferred.)

The reaction solution was poured into a mixture of EtOAc (280 ml) and brine (100 ml). The aqueous layer was separated. The organic layer was washed with saturated NaHCO₃ (120 ml×3 ) and 20% aqueous NaHSO₃ (100 ml×1). The combined aqueous layer was back-extracted with EtOAc (150 ml×2). All of the EtOAc extracts were combined and washed with saturated NaHCO₃ (150 ml×1), half-saturated aqueous NaCl (120 ml×1), brine (150 ml×2 ), dried over Na₂SO₄, filtered, and concentrated to give 67 g of the crude diol. This residue was dissolved in hexane (195 ml) and EtOAc (15 ml), and set aside at room temperature for 2 hours and then in the cold room (4° C.) for 16 hours. The crystals were filtered and washed with 1% EtOAc in hexane (50 ml) and dried in vacuo (house low vac) to give 36 g of the pure diol (title product) (calc. 61% from chlorohydrin) as colorless crystals, mp 50°–52° C. (The crude diol prior to crystallization contained approximately 3% of the hydroxyketone starting material. After crystallization from EtOAc and hexane, the starting material was not detected and the title product was pure by H-NMR.)

(d) (4R-cis)-6-(Chloromethyl)-2,2-dimethyl-1,3-dioxane-4-acetic acid, 1,1-dimethylethyl ester

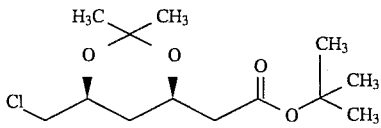

A solution of the diol (R,S)-6-chloro-3,5dihydroxyhexanoic acid, 1,1-dimethylethyl ester prepared in step (c) above (35.7 g) and camphorsulfonic acid (0. 697 g, 0.02 eq) in 2,2-dimethoxypropane (92 ml, 5.0 eq) was stirred at room temperature for 30 minutes in a well-functioning hood. At this point, only a trace mount of diol was present by TLC. (The TLC conditions employed were those described above). The reaction solution was poured into a mixture of EtOAc (100 ml) and saturated $NaHCO_3$ (150 ml) in a separatory funnel. The aqueous layer was separated and extracted with EtOAc (50 ml). The combined EtOAc layer was washed with half-saturated aqueous NaCl (60 ml×1), brine (60 ml×2 ), dried over MgSO4, filtered, and concentrated to give 40.46 g (97%) of the chloroacetonide title product as a colorless liquid.

(e) (4R-cis)-6- [(Acetyloxy )methyl ]-2,2-dimethyl-1,3-dioxane-4-acetic acid, 1,1-dimethylethyl ester

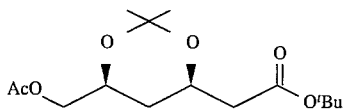

(i) Preparation of tetra-n-butylammonium acetate

Glacial acetic acid (approximately 23.5 ml) was added dropwise to a stirred 40% aqueous solution of tetrabutylammonium hydroxide (252 ml) in a 1 L three-necked, round bottomed flask fitted with an argon inlet and a pH electrode. During the addition of acetic acid the temperature of the reaction was kept below 35° C. When the pH of the solution reached 8.5 the addition of acetic acid was stopped and the solution was concentrated on a rotary evaporator ≦35° C. under high vacuum (about 0.1 mmHg). The resulting semi-solid was azeotropically dried with toluene (4×500 ml) on a rotary evaporator ≦35° C. and then under high vacuum (about 0.1 mmHg) for 24 to 48 hours to afford the white solid (113 grams) tetrabutylammonium acetate. The pH of a solution of 1 gram of the above salt in 2.4 ml of water was 7.66 and 1% aqueous solution was approximately 7.15. The pH of a 1% aqueous solution of tetrabutylammonium acetate is preferably greater than 7.00. (The following conversion to the title compound proceeds at a rapid rate and with a good chemical yield.)

(ii) The displacement reaction

Solid tetrabutylammonium acetate obtained as above (111 g, 0.368 mole) was added in one portion to a mechanically stirred solution of the chloride (4R-cis)-6-(chloromethyl)-2, 2-dimethyl-1,3-dioxane-4-acetic acid, 1,1-dimethylethyl ester prepared in step (d) above (35 g, 0.125 mole) in HPLC grade 1-methyl-2-pyrrolidinone (504 ml) under argon. The resulting solution was stirred at 85° C. (internal temperature). After 30 to 60 minutes the reaction mixture became homogeneous and brown in color. The progress of the reaction was followed by TLC and GC analysis. (TLC: Rf=0.63 for the chloride starting material; $R_f$=0.54 for the title compound (silica gel, Ethyl acetate:Hexane, 1:1, visualization by $Ce(SO_4)_2$ spray). GC: $R_t$=7.20 minutes (starting material) and 8.66 minutes (title compound).) After 11 hours the reaction was completed.

The reaction mixture was cooled to room temperature and poured into pH 7.00 phosphate buffer (4 L) and extracted with heptane (3×1 L). (It was found from another experiment that the reaction may also be quenched with water instead of pH 7.00 buffer without affecting the yield or the quality of the product.) The organic layers were combined and washed with water (1 L), brine, dried over $MgSO_4$, filtered and concentrated under reduced pressure to 1 L and treated with neutral NORIT® (40 grams). The heterogeneous solution was boiled on a water bath for about 2 minutes and filtered hot through a Celite bed on a Buchner funnel. The residue was washed with hot heptane (3×250 ml). The filtrates were combined and concentrated on a rotary evaporator under reduced pressure to afford the title compound as a light yellow solid (32.4 grams, 86%). This material was used in the next step without any further purification.

(f) (4R-cis)-6-(Hydroxymethyl)-2,2-dimethyl-1,3-dioxane-4-acetic acid, 1,1-dimethylethyl ester

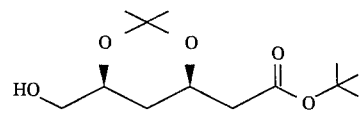

To a solution of (4R-cis)-6- [(acetyloxy)methyl]-2,2-dimethyl-1,3-dioxane-4-acetic acid, 1,1-dimethylethyl ester (32.2 g, 106 mmole), obtained from the above reaction, in methanol (355 ml), was added powdered anhydrous potassium carbonate (7.34 g, 53.3 mmole) in one portion. The resulting heterogeneous solution was stirred vigorously for 30 minutes to complete the hydrolysis. The solution was filtered through a Buchner funnel and concentrated on a rotary evaporator at room temperature under reduced pressure. Concentration of the reaction mixture at room temperature was employed as concentration at a higher temperature led to the formation of a more polar impurity.

The residue was dissolved in water (250 ml) and extracted with ether (3×200 ml). The combined organic layers were washed with water (150 ml), brine (150 ml), dried over $MgSO_4$, filtered and concentrated on a rotary evaporator to furnish the title compound as a dark brown oil (28.43 g). This crude product was distilled using a short path distillation apparatus under vacuum. The following fractions were collected.

| | |
|---|---|
| Fraction 1: 0.97 g | 95–106° C./0.5 mmHg |
| Fraction 2: 24.0 g | 106–116° C./0.4–0.15 mmHg |
| | 95% GC HI |

Fraction 2 contained the title compound along with small amounts of minor impurities as indicated by TLC and $^1$HNMR. This material was therefore redistilled and three fractions were collected.

Fraction 1: 0.5 g 85°–89° C./0.12–0.06 mmHg; 47.3% GC HI

Fraction 2: 1.1 g 89° C./0.08 mmHg; 79.0% GC HI

Fraction 3: 21.1 g 89°–92° C./0.08 mmHg; 98.9% GC HI

Fraction 3 contained the pure title compound (21.1 g, 65% overall yield from the starting material.)

(To avoid the second distillation above, the initial distillation may be carried out through a small Vigreaux column.)

EXAMPLE 2

Preparation of
(4R-cis)-6-(Hydroxymethyl)-2,2-dimethyl-1,
3-dioxane-4-acetic acid, 1,1-dimethylethyl ester (a) (4R-cis)-6-[(Acetyloxy)methyl]-2,2-dimethyl-1,3-dioxane-4-acetic acid, 1,1-dimethylethyl ester

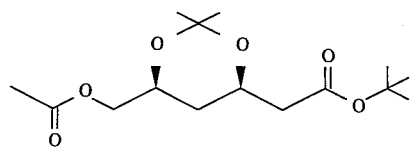

Solid tetra-n-butylammonium acetate prepared in step (e) (i) of Example 1 above (106.2 g, 0,352 mole) was added in one portion to a mechanically stirred solution of the chloride (4R-cis)-6-(chloromethyl)-2,2-dimethyl-1,3-dioxane-4-acetic acid, 1,1-dimethylethyl ester prepared in step (d) of Example 1 above (32.7 g, 0. 117 mole) in HPLC grade 1-methyl-2-pyrrolidinone (471 ml) under argon. The resulting solution was stirred at 85° C. (internal temperature). After 30 to 60 minutes the reaction mixture became homogeneous and brown in color. The progress of the reaction was followed by TLC and GC analysis. (TLC: $R_f$=0.54 for the title compound; $R_f$=0.63 for the chloride starting material (silica gel, Ethyl acetate: Hexane, 1:1, visualization by Ce(SO$_4$)$_2$ spray).) After 9 hours the reaction was completed.

The reaction mixture was cooled to room temperature and poured into water (4 L) and extracted with heptane (3×1 L). The organic layers were combined and washed with water (1 L), brine, dried over MgSO$_4$, filtered and concentrated under reduced pressure to furnish 31.5 grams of a brown solid. It was dissolved in heptane (500 ml) and treated with neutral NORIT® (40 grams). The heterogeneous solution was boiled on a water bath for a few minutes and filtered hot through a celite bed on a Buchner funnel. The residue was washed with hot heptane (3×250 ml).

The filtrates were combined and concentrated on a rotary evaporator under reduced pressure to afford the title compound as a light yellow solid (31.1 grams). This solid was dissolved in hot heptane (60 ml) and allowed to cool slowly to room temperature. During this time off-white crystals began to form. The mixture was kept in the freezer (–20° C.) for 1 hour and the crystals were then filtered, washed with cold heptane (75 ml) and dried in vacuo (approximately 1 mmHg) at room temperature for 3 hours to furnish 24.22 grams (68%) of the title compound as off-white crystals. m.p. 64°–64.5° C.; TLC: Rf=0.54 (silica gel, Ethyl acetate: Hexane, 1:1, visualization by Ce (SO$_4$ )$_2$ spray); GC: $R_t$=7.20 minutes (chloride starting material) and 8.66 minutes (title compound). 6% of the title compound was also collected as a second crop. The mother liquor (2.60 g) still contained about 20% of the title product as determined by TLC.

(b) (4R-cis)-6-(Hydroxymethyl)-2,2-dimethyl-1,3-dioxane-4-acetic acid, 1,1-dimethylethyl ester

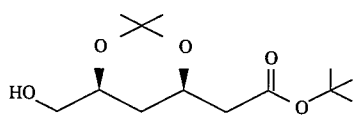

To a solution of (4R-cis)-6-[(acetyloxy)methyl]-2,2-dimethyl-1,3-dioxane-4-acetic acid, 1,1-dimethylethyl ester obtained in step (a) above (22.65 g, 75 mmole) in methanol (250 ml) was added powdered anhydrous potassium carbonate (5.17 g, 37.5 mmole) in one portion. The resulting heterogeneous solution was stirred vigorously for 30 minutes to complete the hydrolysis. The progress of the reaction was followed by TLC and GC analysis. (TLC: Rf=0.54 for acetyloxy starting material; Rf=0.26 for the title compound (silica gel, Ethyl acetate:Hexane, 1:1, visualized by Ce(SO$_4$)$_2$ spray).

The solution was filtered through a Buchner funnel and concentrated on a rotary evaporator at room temperature under reduced pressure. Room temperature was employed as concentration of the reaction mixture at a higher temperature led to the formation of a more polar impurity. The residue was dissolved in water (250 ml) and extracted with ether (3×2 00 ml).

The combined organic layers were washed with water (150 ml), brine (150 ml), dried over MgSO$_4$, filtered and concentrated on a rotary evaporator to furnish the title compound as a light yellow oil (19.2 g) in 98% yield. (TLC: Rf=0.26 for the title compound; silica gel, Ethyl acetate-:Hexane, 1:1, visualized by Ce(SO$_4$)$_2$ spray. GC: $R_t$=8.66 min. (acetyloxy starting material) and 7.32 min. (title compound).)

EXAMPLE 3

Preparation of
(4R-cis)-6-(Hydroxymethyl)-2,2-dimethyl-1,3-dioxane-4-acetic acid, 1,1-dimethylethyl ester (a) (4R-cis)-6- [(Benzoyloxy)methyl]-2,2-di-methyl-1,3-dioxane-4-acetic acid, 1,1-dimethylethyl ester

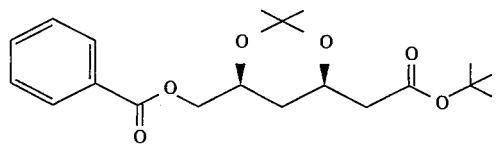

(i) Preparation of tetra-n-butylammonium benzoate

Benzoic acid (approximately 38 grams) was added portionwise to a stirred 40% aqueous solution of tetrabutylammonium hydroxide (200 ml) in a 1 L three-necked, round-bottomed flask fitted with an argon inlet and a pH electrode. During the addition of benzoic acid the temperature of the reaction was kept below 35° C. When the pH of the solution reached 8.5 the addition of benzoic acid was stopped and the solution was concentrated on a rotary evaporator at ≦35° C. under high vacuum (about 0.1 mmHg). The resulting semi-solid was azeotropically dried with toluene (4×500 ml) on a rotary evaporator at ≦35° C. and then under high vacuum (about 0.1 mmHg) for 24 to 48 hours to afford as a white solid (114 grams) tetrabutylammonium benzoate. KF analysis indicated the presence of 1.20% water in this reagent. The pH of a solution of 2 grams of the above salt in 4 ml of water was 8.29 and a 1% aqueous solution was approximately 7.05. The pH of a 1% aqueous solution of tetrabutylammonium benzoate is preferably greater than 7.00. (The conversion to the title compound described following proceeds rapidly and with a good chemical yield.)

(ii) The displacement reaction

Solid tetrabutylammonium benzoate obtained as above (126.47 g, 0.348 mole) was added in one portion to a mechanically stirred solution of the chloride (4R-cis)-6-(chloromethyl)-2,2-dimethyl-1,3-dioxane-4-acetic acid, 1,1-dimethylethyl ester prepared as in step (d) of Example 1 above (32.3 g, 0.116 mole) in HPLC grade 1-methyl-2- pyrrolidinone (465 ml) under argon. The resulting solution was stirred at 100° C. (internal temperature). After 30 to 60 minutes the reaction mixture became homogeneous and brown in color. The progress of the reaction was followed by TLC and GC analysis (TLC: $R_f=0.47$ for the chloride starting material; $R_f=0.35$ for the title compound (silica gel, Ether:Hexane, 4:6, visualization by Ce $(SO_4)_2$ spray). After 6.5 hours the reaction was completed.

The reaction mixture was cooled to room temperature and poured into water (4 L) and extracted with heptane (3×1 L). The organic layers were combined and washed with water (1 L), brine, dried over $MgSO_4$, filtered and concentrated under reduced pressure to furnish 42.2 grams of a yellow solid. This solid was dissolved in hot heptane (100 ml) and allowed to cool slowly to room temperature. During this time off-white crystals began to form. After standing at room temperature for two hours and at −20° C. (freezer) for one hour the crystals were filtered, washed with cold heptane (75 ml) and dried in vacuo (about 1 mmHg) at room temperature for 3 hours to furnish 33.00 grams of the title compound in 78% yield. An additional 3% of the title product was also collected as a second crop. The mother liquor (4.68 grams) still contained the title product (approximately 75%) as determined by TLC. (TLC: $R_f=0.35$ Silica gel, Ether:Hexane, 4:6, visualization by Ce$(SO_4)_2$ spray; GC: $R_t=5.57$ minutes (chloride starting material) and 11.52 minutes (title compound).)

(b) (4R-cis)-6-(Hydroxymethyl)-2,2-dimethyl-1,3-dioxane-4-acetic acid, 1,1-dimethylethyl ester

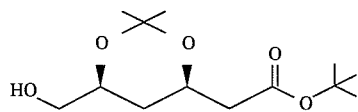

To a solution of (4R-cis)-6-[(benzoyloxy)methyl]-2,2-dimethyl-1,3-dioxane-4-acetic acid, 1,1-dimethylethyl ester prepared in step (a) above (30.00 g, 82.4 mmole) in methanol (275 ml) was added granular anhydrous potassium carbonate (5.68 g, 41.2 mmole) in one portion. The resulting heterogeneous solution was stirred vigorously for 2 hours to complete the hydrolysis. The progress of the reaction was followed by TLC analysis. (TLC: $R_f=0.31$ for the benzoyloxy starting material, $R_f=0.17$ for the title compound (silica gel, Ether:Hexane, 1:1, visualized by Ce$(SO_4)_2$ spray).

The solution was filtered through a Buchner funnel and concentrated on a rotary evaporator at room temperature under reduced pressure. Room temperature was employed as concentration of the reaction mixture at a higher temperature led to the formation of a more polar impurity (uncharacterized). The residue was dissolved in water (500 ml) and extracted with ether (4×250 ml). The combined organic layers were washed with water (3×150 ml), brine (150 ml), dried over $MgSO_4$, filtered and concentrated on a rotary evaporator to furnish the title compound along with methyl benzoate as a colorless oil (32.6 g). This crude product was distilled using a short path distillation apparatus under high vacuum to remove the methyl benzoate. The following fractions were collected.

| Fraction 1 | 5.16 g |         | 42° C./0.25 mmHg   |
| ---------- | ------ | ------- | ------------------ |
| Fraction 2 | 2.71 g |         | 50° C./0.25 mmHg   |
| Fraction 3 | 1.80 g |         | 52° C./0.25 mmHg   |

-continued

| Fraction 4 | 0.26 g  |         | 65° C./0.25 mmHg   |
| ---------- | ------- | ------- | ------------------ |
| Fraction 5 | 0.98 g  |         | 108° C./0.25 mmHg  |
| Fraction 6 | 0.56 g  | (2.6%)  | 108° C./0.25 mmHg  |
| Fraction 7 | 18.09 g | (84.4%) | 108–111° C./0.25 mmHg |

Fraction 1 to Fraction 4 contained mainly methyl benzoate. Fraction 5 was a mixture of methyl benzoate (minor) and the title compound (major). Fraction 6 and Fraction 7 contained only the title compound ($^1$HNMR).

Fraction 7: GC: HI 99.00%, TLC: $R_f=0.17$ for the title compound, Silica gel, Ether:Hexane, 1:1, visualized by Ce$(SO_4)_2$ spray; GC: $R_t=7.32$ minutes (title compound).

EXAMPLE 4

Preparation of (4R-cis)-6-(Hydroxymethyl)-2,2-dimethyl-1,3-dioxane-4-acetic acid, 1,1-dimethylethyl ester (a) (S)-6-Bromo-5-hydroxy-3-oxohexanoic acid, 1,1-dimethylether ester

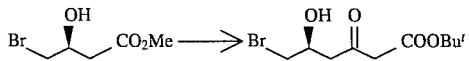

A flame dried 3 L three-necked round bottom flask was charged with tetrahydrofuran (THF) (distilled, 275 ml) and lithium hexamethyldisilazide (LiHMDS) (980 ml, 3.5 eq, 1M solution in THF) at −78° C. The addition of THF was to prevent the LiHMDS from precipitation. To this light brown solution was slowly added tert-butyl acetate ($CH_3CO_2Bu^t$) (151 ml, 4.0 eq) over a period of 10 minutes at −78° C. At the end of the addition, the solution was stirred for another 40 minutes at −78° C. To this light brown homogeneous solution was added a solution of the bromohydrin (S)-4-bromo-3-hydroxybutanoic acid methyl ester (55 g, 0.028 mole, CHIRON, used as purchased) in THF (40 ml) over a period of 20 minutes. The addition was slightly exothermic. The internal temperature climbed from −78° C. to −74° C. during the addition.

The resultant solution was stirred at −78° C. for an additional 1 hour, and then −50° C. for 1 hour. At this point TLC indicated complete reaction. (TLC: silica gel; Ethyl acetate:Hexane; 1:1; $R_f=0.56$, UV visualization for the title product; $R_f=0.55$, PMA visualization for the bromohydrin starting material.) The reaction solution was slowly transferred via a cannula to a stirred solution of glacial acetic acid (220 ml) in THF (400 ml) at 0° C. The resulting yellow solution was poured into a separatory funnel containing $H_2O$ (800 ml). The aqueous layer was separated and extracted with ethyl acetate (180 ml×2). The combined organic layer was washed with 1N HCl (300 ml×2), and half-saturated NaCl (300 ml×1). The combined HCl and NaCl washings were back extracted with ethyl acetate (300 ml×2). All the ethyl acetate extracts were combined and washed with saturated $NaHCO_3$ (400 ml×2), half-saturated NaCl (400 ml×1) and brine (300 ml×2), dried over $Na_2SO_4$, filtered and concentrated to give approximately 79 g of the hydroxyketone title product as a brown oil (about 100%). (H-NMR indicated that no starting material remained. The title product was about 80% pure by H-NMR and TLC (same conditions as previously).) The product was used for the next step without any further purification.

(b) (R,S) -6-Bromo-3,5-dihydroxyhexanoic acid, 1,1-dimethylethyl ester

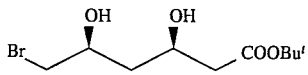

The crude hydroxyketone obtained in step (a) above (79.0 g) was dissolved in THF (1.26 ml) and methanol (MeOH) (HPLC grade, 605 ml) at −78° C. To this brown solution was added methoxydiethylborane ($Et_2BOMe$) (299 ml, 1M solution in THF) over a period of 25 minutes. The addition was slightly exothermic and the solution became cloudy. At the end of the addition, the reaction solution was stirred for an additional 20 minutes. To this cloudy solution was added solid $NaBH_4$ (11 g, 1.15 eq.) portionwise over a period of 35 minutes. The addition generated a large amount of hydrogen gas. Good stirring was employed to prevent frothing. The resultant suspension was stirred at −78° C. for 4 hours. The reaction mixture was slowly added via a cannula to a stirred solution of glacial acetic acid (106 ml) in ethyl acetate (800 ml) at 0° C. The organic solution was separated and washed with half-saturated NaCl (400 ml×2) and saturated $NaHCO_3$ (400 ml×4). The combined aqueous washings were back extracted with ethyl acetate (400 ml×2). All the ethyl acetate extracts were combined and washed with half-saturated aqueous NaCl (400 ml×1), brine (400 ml×2), dried over $Na_2SO_4$, filtered, and concentrated to give 85 g of the crude product as a mixture of the diol title product and the corresponding boron complex. At this point, the boron complex was the major component in the crude residue and about 3% of the starting material remained by H-NMR. (TLC: silica gel; Ethyl acetate :Hexane; 1:1, $R_f$=0.81, for the boron complex; $R_f$=0.44, for the diol title product; $R_f$=0.56, for the hydroxyketone starting material.)

The above crude product (85 g) was dissolved in THF (400 ml) and water (350 ml, deionized). To this solution was added 30% aqueous $H_2O_2$ (75 ml). The addition of $H_2O_2$ was exothermic and ice-water cooling was employed to control the temperature between 24° C. and 30° C. The pH of the resulting solution was about 6. Addition of 1N NaOH (approximately 20 ml) followed to maintain the pH of this solution equal to 7. The resultant mixture was stirred for an additional 30 minutes at room temperature. The solution was maintained at pH 7 throughout the reaction period.

The reaction solution was poured into a mixture of ethyl acetate (275 ml) and brine (110 ml). The aqueous layer was separated. The organic layer was washed with saturated $NaHCO_3$(400 ml×3 ) and 10% aqueous $NaHSO_3$ (200 ml×1). The combined aqueous layer was back extracted with ethyl acetate (200 ml×2). All the ethyl acetate extracts were combined and washed with saturated $NaHCO_3$ (300 ml×1), half-saturated aqueous NaCl (200 ml×1) and brine (300 ml×3), dried over $Na_2SO_4$, filtered and concentrated to give 70 g of the crude diol title product. This residue was dissolved in hexane (180 ml) and ethyl acetate (8 ml), seeded and set aside at room temperature for 2 hours and then in the cold room (4° C.) for 16 hours. The crystals were filtered and washed with 1% ethyl acetate in hexane (30 ml) and dried in vacuo (low house vac) to give 27 g of the pure diol title product (calc. 34% from (S)-4-bromo-3-hydroxybutanoic acid methyl ester) as colorless crystals, mp 43.5°–46° C.

(c) (4R-cis)-6-(Bromomethyl)-2,2-dimethyl-1,3-dioxane-4-acetic acid, 1,1-dimethylethyl ester

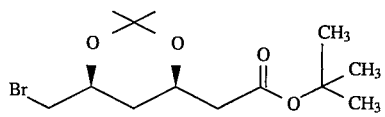

A solution of the diol obtained in step (b) above (25.4 g, 90 mmol) and camphorsulfonic acid (0.209 g, 0.01 eq) in 2,2-dimethoxypropane (55 ml, 5.0 eq) (note: as 2,2-dimethoxypropane may cause eye irritation, operations with this material should be carried out in a well-functioning hood) was stirred at room temperature for 40 minutes. At this point, only a trace amount of the diol starting material was present by TLC. (TLC conditions as previously described). The reaction solution was poured into a mixture of ethyl acetate (300 ml) and saturated $NaHCO_3$ (300 ml) in a separatory funnel. The aqueous layer was separated and extracted with ethyl acetate (50 ml). The combined ethyl acetate layer was washed with half-saturated aqueous NaCl (60 ml×1), brine (60 ml×2 ), dried over $MgSo_4$, filtered, and concentrated to give 27.0 g (97%) of the bromoacetonide title product as a pale yellow liquid.

| | Elemental Analysis (%) $C_{13}H_{23}BrO_4$ | |
|---|---|---|
| | Calc. | Found |
| C | 48.31 | 48.80 |
| H | 7.17 | 7.29 |
| Br | 24.72 | 24.85 |

$[\alpha]_D$=+7.78 (c 1.0, MeOH), $[\alpha]_{365}$=+31.52 (c 1.0, MeOH) TLC:$R_f$=0.55; Ethyl acetate:Hexane; 3:7; Silica gel; UV and PMA Visualization; HPLC: HI=89.5, II 0.4 for anti acetonide, II 0.2 for hydroxyketone and II 9.9 for total unknowns. (HI stands for Homogeneity Index; II stands for Impurity Index).

(d) (4R-cis) -6-[(Acetyloxy)methyl]-2,2-dimethyl-1,3-dioxane-4-acetic acid, 1,1-dimethylethyl ester

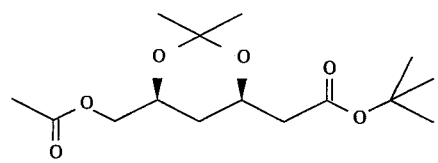

Solid tetrabutylammonium acetate (62.4 g, 0.207 mole, commercially available reagent was used) was added in one portion to a stirring solution of the bromoacetonide obtained in step (c) above (22.3 g, 0.068 mole) in 1-methyl-2-pyrrolidinone (276 ml, commercially available HPLC grade, used as purchased) under an argon atmosphere. The resulting solution was stirred at 90° C. (external temperature) for 1 hour (after a few minutes the reaction mixture became brown in color) to complete the reaction. (The progress of the reaction was followed by TLC, $R_f$=0.48 for the title product; $R_f$=0.63 for the bromoacetonide starting material (Silica gel, Ethyl acetate:Hexane, 1:1, visualization by $Ce(SO_4)_2$ spray).) The reaction mixture was cooled to room temperature and poured into water (1.5 L) and extracted with heptane (4×800 ml). The organic layers were combined and washed with water, brine, dried over $MgSO_4$, filtered and concentrated under reduced pressure to furnish 18.45 grams of a brown solid. It was dissolved in heptane (250 ml) and treated with neutral NORIT® (25 grams).

The heterogeneous solution was boiled on a water bath for 5 minutes and filtered hot through a celite bed on a Buchner funnel. The residue was washed with hot heptane (3×150 ml). The filtrates were combined and concentrated on a rotary evaporator under reduced pressure to afford the title product as a light yellow solid (17.6 grams). This solid was dissolved in hot heptane (40 ml) and allowed to cool slowly to room temperature and during this time off-white crystals began to form. It was kept in the cold room (−5° C.) overnight and the crystals were filtered, washed with cold heptane (50 ml) and dried in vacuo (about 1 mmHg) at room temperature for 3 hours to furnish 14.47 grams (69.5%) of the title product as off-white crystals. An additional 7.5% of the title product was also collected as a second crop. m.p. 64°–65° C.; TLC: $R_f$=0.48 (Silica gel, Ethyl acetate:Hexane, 1:1 visualization by $Ce(SO_4)_2$ spray).

| Elemental Analysis (%) $C_{15}H_{26}O_6$ | | |
| --- | --- | --- |
| | Calc. | Found |
| C | 59.58 | 59.64 |
| H | 8.67 | 8.94 |

(e) (4R-cis)-6-(Hydroxymethyl)-2,2-dimethyl-1,3-dioxane-4-acetic acid, 1,1-dimethylethyl ester (4R-cis)-6-[(Acetyloxy)methyl]-2,2-dimethyl-1,3-dioxane-4-acetic acid, 1,1-dimethylethyl ester obtained in step (d) above is converted to the title product according to the procedure of Example 1, step (f).

What is claimed is:

1. A method for the preparation of a compound of the formula VII:

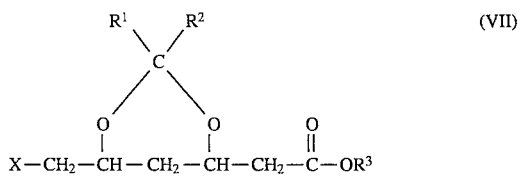

where

X is a halogen atom;

$R^1$ and $R^2$ are each independently hydrogen, an alkyl group, a cycloalkyl group, an aryl group or, taken together with the carbon atom to which they are attached, form a cycloalkyl group; and $R^3$ is hydrogen, an alkyl group or an aryl group, or a pharmaceutically acceptable salt thereof, comprising the step of reacting a compound of the formula V:

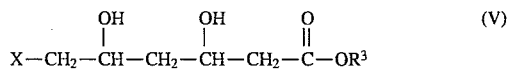

where

X and $R^3$ are as defined in the formula VII, or a pharmaceutically acceptable salt thereof, with a compound of the formula VIa, VIb or VIc:

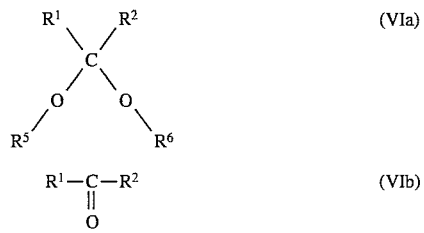

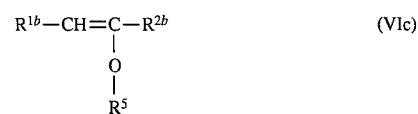

where $R^1$ and $R^2$ are as defined in the formula VII;

$R^{1b}$ and $R^{2b}$ are each independently hydrogen, an alkyl group, a cycloalkyl group, an aryl group or, taken together with the carbon atoms to which they are attached, form a 1,2-cycloalkenyl group; and $R^5$ and $R^6$ are each independently an alkyl group, in the presence of an acidic condensation agent, wherein alkyl employed herein alone or as part of another group has from 1 to 21 carbons;

cycloalkyl employed herein alone or as part of another group has from 3 to 21 carbons;

aryl employed herein alone or as part of another group has from 6 to 12 carbons;

cycloalkenyl employed herein alone or as part of another group has from 3 to 21 carbons.

2. The method of claim 1, wherein a compound or pharmaceutically acceptable salt thereof having the stereoisomeric configuration Va is employed:

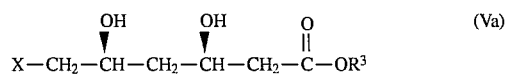

and wherein a compound or pharmaceutically acceptable salt thereof having the stereoisomeric configuration VIIa is prepared:

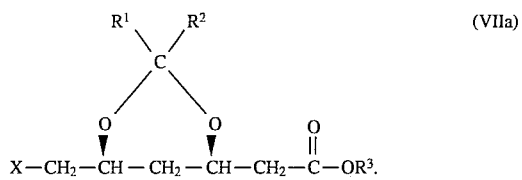

3. A compound of the formula VII:

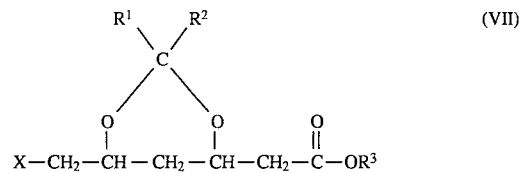

where

X is a halogen atom;

$R^1$ and $R^2$ are each independently hydrogen, an alkyl group, a cycloalkyl group, an aryl group or, taken together with the carbon atom to which they are attached, form a cycloalkyl group; and $R^3$ is hydrogen, an alkyl group, or an aryl group, or a pharmaceutically acceptable salt thereof, wherein alkyl employed herein alone or as part of another group has from 1 to 21 carbons;

cycloalkyl employed herein alone or as part of another group has from 3 to 21 carbons;

aryl employed herein alone or as part of another group has from 6 to 12 carbons.

4. The compound as defined in claim 3, wherein said compound or pharmaceutically acceptable salt thereof has the stereoisomeric configuration VIIa:

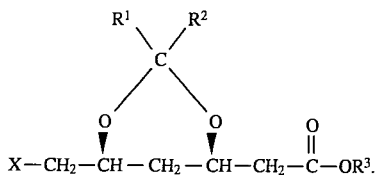

(VIIa)

5. A method for the preparation of a compound of the formula VIII:

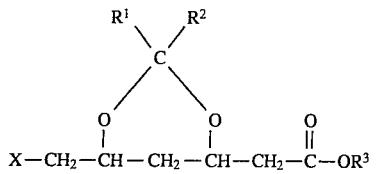

(VIII)

where

R$^1$ and R$^2$ are each independently hydrogen, an alkyl group, a cycloalkyl group, an aryl group or, taken together with the carbon atom to which they are attached, form a cycloalkyl group;

R$^3$ is hydrogen, an alkyl group or an aryl group; and

R$^7$ is an alkyl group or an aryl group;

or a pharmaceutically acceptable salt thereof, comprising the step of displacing the group X of a compound of the formula VII:

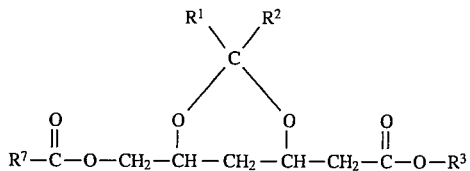

(VII)

where x is a halogen atom; and

R$^1$, R$^2$ and R$^3$ are as defined in the formula VIII, or a pharmaceutically acceptable salt thereof, with an acyloxy group of the formula —O—C(O)—R$^7$, by use of a displacement agent, wherein alkyl employed herein alone or as part of another group has from 1 to 21 carbons;

cycloalkyl employed herein alone or as part of another group has from 3 to 21 carbons;

aryl employed herein alone or as part of another group has from 6 to 12 carbons.

6. The method of claim 5, wherein a compound or pharmaceutically acceptable salt thereof having the stereoisomeric configuration VIIa is employed:

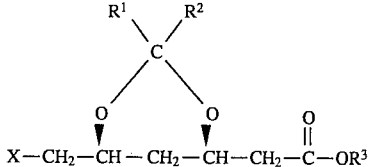

(VIIa)

and wherein a compound or pharmaceutically acceptable salt thereof having the stereoisomeric configuration VIIa is prepared:

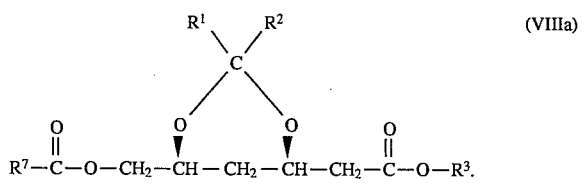

(VIIIa)

7. The method of claim 5, wherein a compound of the formula IX:

(IX)

where

M is a metal or an ammonium group; and R$^7$ is as defined for the formula VIII, is employed as said displacement agent.

8. A compound of the formula VIII:

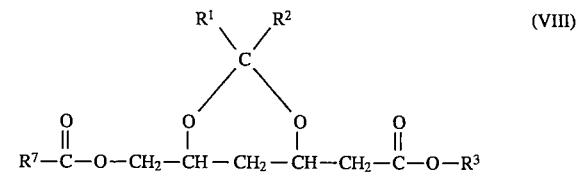

(VIII)

where

R$^1$ and R$^2$ are each independently hydrogen, an alkyl group, a cycloalkyl group, an aryl group or, taken together with the carbon atom to which they are attached, form a cycloalkyl group;

R$^3$ is hydrogen, an alkyl group or an aryl group; and

R$^7$ is an alkyl group, of a pharmaceutically acceptable salt thereof, wherein alkyl employed herein alone or as part of another group has from 1 to 21 carbons;

cycloalkyl employed herein alone or as part of another group has from 3 to 21 carbons;

aryl employed herein alone or as part of another group has from 6 to 12 carbons.

9. The compound as defined in claim 8, wherein said compound or pharmaceutically acceptable salt thereof has the stereoisomeric configuration VIIIa:

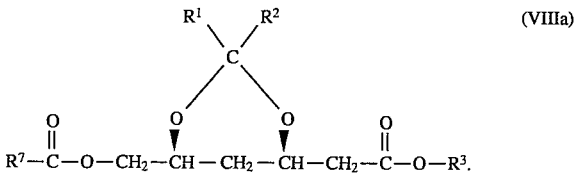

(VIIIa)

10. A method for the preparation of a compound of the formula I:

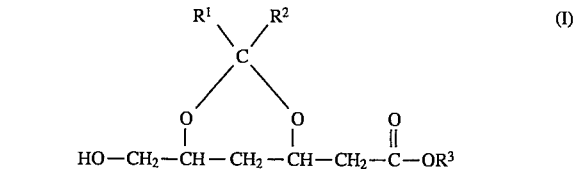

(I)

where

R$^1$ and R$^2$ are each independently hydrogen, an alkyl group, a cycloalkyl group, an aryl group or, taken together with the carbon atom to which they are attached, form a cycloalkyl group; and R$^3$ is hydrogen, an alkyl group, or an aryl group;

or a pharmaceutically acceptable salt thereof:

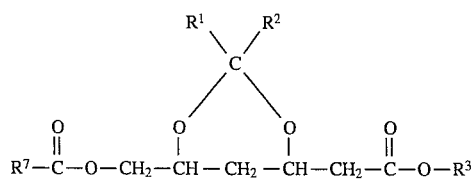
(VIII)

where

R$^1$, R$^2$ and R$^3$ are as defined in the formula I, and (i) R$^7$ is an alkyl group; or (ii) said hydrolysis is conducted employing a mild base and/or a mildly basic medium and R$^7$ is an alkyl group or an aryl group, wherein alkyl employed herein alone or as part of another group has from 1 to 21 carbons;

cycloalkyl employed herein alone or as part of another group has from 3 to 21 carbons;

aryl employed herein alone or as part of another group has from 6 to 12 carbons.

11. The method of claim 10, wherein a compound or pharmaceutically acceptable salt thereof having the stereoisomeric configuration VIIIa is employed:

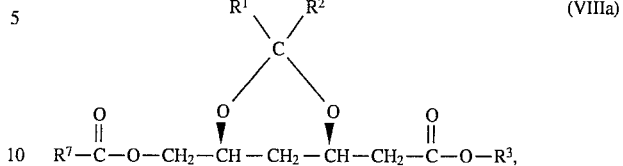
(VIIIa)

and wherein a compound or pharmaceutically acceptable salt thereof having the stereoisomeric configuration Ia is prepared:

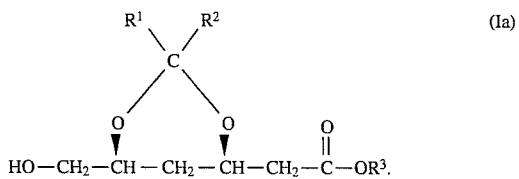
(Ia)

* * * * *